US008663339B2

(12) United States Patent
Inschlag et al.

(10) Patent No.: US 8,663,339 B2
(45) Date of Patent: Mar. 4, 2014

(54) ADJUSTING DEVICE AND METHOD FOR OPERATING AN ADJUSTING DEVICE

(75) Inventors: Josef Inschlag, St. Lorenz am Wechsel (AT); Marcus Eder, Vienna (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 0 days.

(21) Appl. No.: 13/575,271

(22) PCT Filed: Jan. 6, 2011

(86) PCT No.: PCT/EP2011/000022
§ 371 (c)(1),
(2), (4) Date: Jul. 25, 2012

(87) PCT Pub. No.: WO2011/088964
PCT Pub. Date: Jul. 28, 2011

(65) Prior Publication Data
US 2012/0290101 A1 Nov. 15, 2012

(30) Foreign Application Priority Data
Jan. 25, 2010 (DE) .......................... 10 2010 005 690

(51) Int. Cl.
*A61F 2/48* (2006.01)
*H02K 7/10* (2006.01)
(52) U.S. Cl.
USPC .................. 623/24; 623/57; 310/77; 188/162
(58) Field of Classification Search
USPC ............. 310/77, 103, 12.24; 188/162; 623/24
See application file for complete search history.

(56) References Cited

U.S. PATENT DOCUMENTS

| 5,062,855 A | 11/1991 | Rincoe |
| 5,444,318 A * | 8/1995 | Stumpf .......................... 310/77 |
| 7,867,287 B2 | 1/2011 | Puchhammer |
| 2008/0097269 A1 | 4/2008 | Weinberg et al. |

FOREIGN PATENT DOCUMENTS

| DE | 102005061313 A1 | 8/2007 |
| EP | 1962731 B1 | 11/2009 |
| WO | 9641383 A1 | 12/1996 |
| WO | 2006076164 A2 | 7/2006 |
| WO | 2007063266 A1 | 6/2007 |

OTHER PUBLICATIONS

Bacher, Johann, et al., "Actions to increase the Cogging Torque and Effects of the increased Cogging Torque to Permanent Magnet DC Motors," European Conference on Power Electronics and Applications, Dresden, Germany, Sep. 11-14, 2005, ISBN: 978-90-75815-09-2, pp. 1-7.
PCT International Search Report for International Application No. PCT/EP2011/000022, mailed Apr. 19, 2011.

* cited by examiner

*Primary Examiner* — Bruce E Snow
(74) *Attorney, Agent, or Firm* — Holland & Hart LLP

(57) ABSTRACT

The invention relates to an adjusting device for a prosthetic device, having a drive (1) for adjusting at least one first component of the prosthetic device relative to a second component, wherein the drive (1) is designed as a permanent magnet electric motor and comprises a stator (4) having exciter coils (3) and a rotor (2) having at least one permanent magnet is an armature magnet (5). At least one holding magnet (6) in the form of a permanent magnet is arranged on the stator (4) to form a cogging torque for the rotor (2).

19 Claims, 3 Drawing Sheets

ADJUSTING DEVICE AND METHOD FOR OPERATING AN ADJUSTING DEVICE

Figure 1:
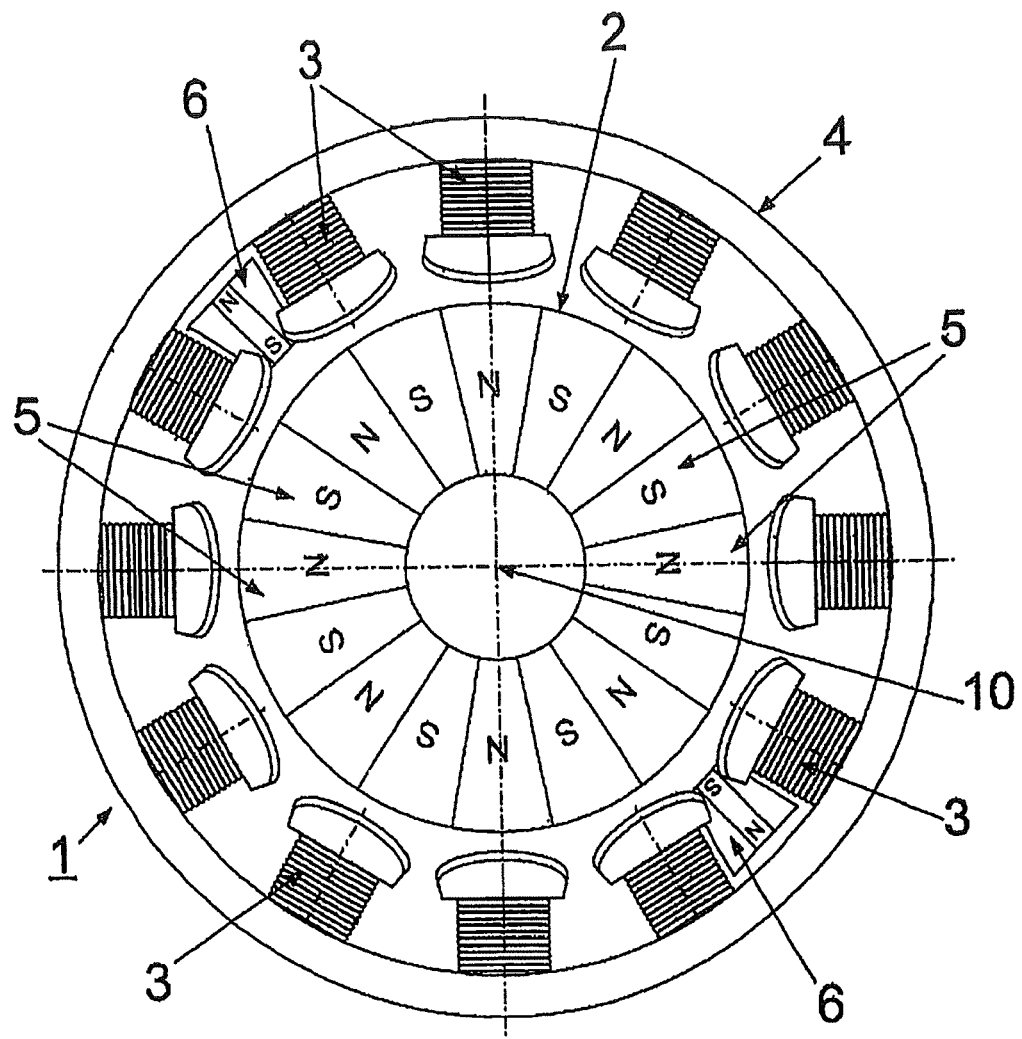

The invention relates to an adjusting device for a prosthetic device, with a drive for adjusting at least one first component of the prosthetic device relative to a second component, wherein the drive is designed as a permanent-magnet electric motor and has a stator with exciter coils and a rotor with at least one permanent magnet as armature magnet. The application further relates to a prosthetic device with an adjusting device of this kind, and to a method for operating an adjusting device of this kind.

Adjustment drives are used extensively in orthopedics, for example in driven prostheses such as prosthetic hands or prosthetic elbows. In these, provision is made that the adjusting device is arranged on one component of the prosthesis and moves a second component relative to the first component. In this way, it is possible, for example, to move a prosthetic lower arm relative to an upper arm stump. Likewise, in a prosthetic hand, the prosthetic fingers can be moved, for example in order to perform a gripping movement.

So as not to have to leave the drive switched on in order to maintain the position that has been reached, devices are provided for mechanically blocking the components relative to each other. Such devices can be brakes, which lock the components in the position that has been reached. The locking or blocking by mechanical components has the disadvantage of high production costs, which result mainly from the increased costs of materials and the larger number of parts. In addition, mechanical components suffer wear, which can lead to increased maintenance costs, and they need a relatively large installation space.

DE 10 2005 061 313 A1 describes a prosthetic hand with a chassis on which several prosthetic fingers are mounted in an articulated manner, and, by means of a drive, the prosthetic fingers are movable relative to the chassis about at least one pivot axis. The drive is designed as an electric motor.

The object of the present invention is to make available an adjusting device for a prosthetic device, a prosthetic device itself, and a method for operating an adjusting device, by which the described advantages are avoided.

According to the invention, this object is achieved by an adjusting device, a prosthetic device and a method according to the independent claims. Advantageous embodiments and developments of the invention are set forth in the dependent claims.

The adjusting device according to the invention for a prosthetic device, with a drive for adjusting at least one first component of the prosthetic device relative to a second component, wherein the drive is designed as a permanent-magnet electric motor and has a stator with exciter coils and a rotor with at least one permanent magnet as armature magnet, is characterized in that at least one holding magnet in the form of a permanent magnet is arranged on the stator in order to provide a cogging torque for the rotor. This has the effect that, even after the exciter coils have been switched off, for example when the motor is switched off after a prosthetic hand has been closed, the attained position of the components relative to each other is maintained. The holding magnet interacts with the permanent magnet of the rotor in such a way that a cogging torque is provided, such that the rotor is maintained in the attained position, if appropriate after a necessary orientation of the rotor to the holding magnet. The cogging torque of the permanent-magnet electric motor is thus increased, such that the drive is blocked after the excitation voltage has been switched off. This happens without additional expenditure of energy, without mechanical wear, and without increased outlay on structural parts. The greater the magnetic forces between the holding magnet and the armature magnet, the greater the cogging torque, such that a rotation of the motor by application of external forces up to a defined torque is no longer possible. The extent of the cogging torque can be adjusted by the choice of magnets.

Provision can be made that a plurality of holding magnets are arranged, spaced apart from one another, on the stator, preferably between the exciter coils, in order to increase the cogging torque and also in order to avoid uneven running of the motor in conventional operation, i.e. during the adjustment. In order to avoid uneven running of the motor, the holding magnets can be distributed uniformly in relation to one another in the circumferential direction, and they can also be arranged at uniform radial distances from the rotation axis, i.e. can lie on a common circumference.

Likewise, a plurality of armature magnets can be arranged in the rotor, with alternating polarity about the circumference, which increases the synchronous running and also increases the positioning accuracy of the adjusting device, since there is then a greater likelihood that a holding magnet with suitable polarity is oriented opposite a corresponding armature magnet.

In order to compensate for the increased cogging torque by the holding magnet or the holding magnets during normal operation of the motor, the effect of the magnet is compensated by superposing a constant field on the rotary field. For this purpose, suitable devices are provided that can compensate for the cogging torque during the adjustment, for example a suitably arranged and configured electromagnet. This electromagnet can also be the stator itself. Thus, the stator winding of the electric motor can be used for compensation of the magnetic field of the holding magnet. The constant field for the compensation can be provided either by additional devices or preferably by superposing a direct current on the motor current, i.e. on the rotary field.

The prosthetic device with an adjusting device of the kind described above can be designed as a prosthetic hand or prosthetic elbow, wherein the first component can be designed as a prosthetic finger and the second component as a chassis. It is likewise possible that the first component is designed as a lower arm socket and the second component as an upper arm socket or a receiving device for an upper arm stump.

The drive is preferably mounted on a chassis and can be coupled to the prosthetic finger or to the lower arm socket via a gear.

The method for operating an adjusting device of the kind described above is characterized in that, when a rotary field is applied to drive the rotor, at least one constant field is superposed on the rotary field, such that the cogging torque generated by the holding magnet or the holding magnets is compensated. The constant field can in this case be provided, for example, via an electromagnet.

Figure 2:
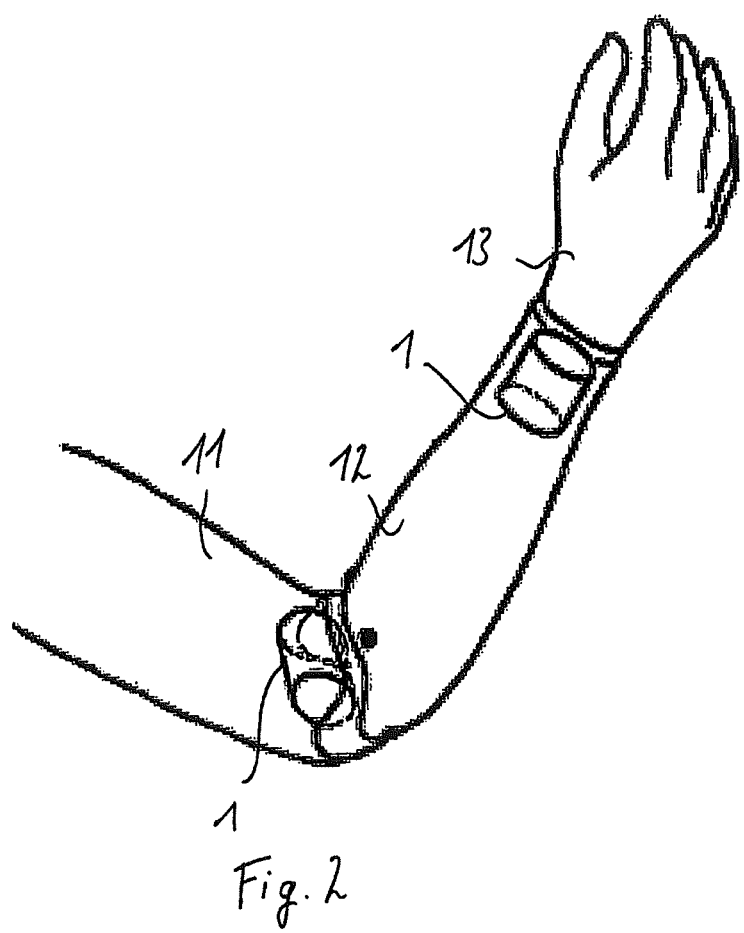
Figure 3:
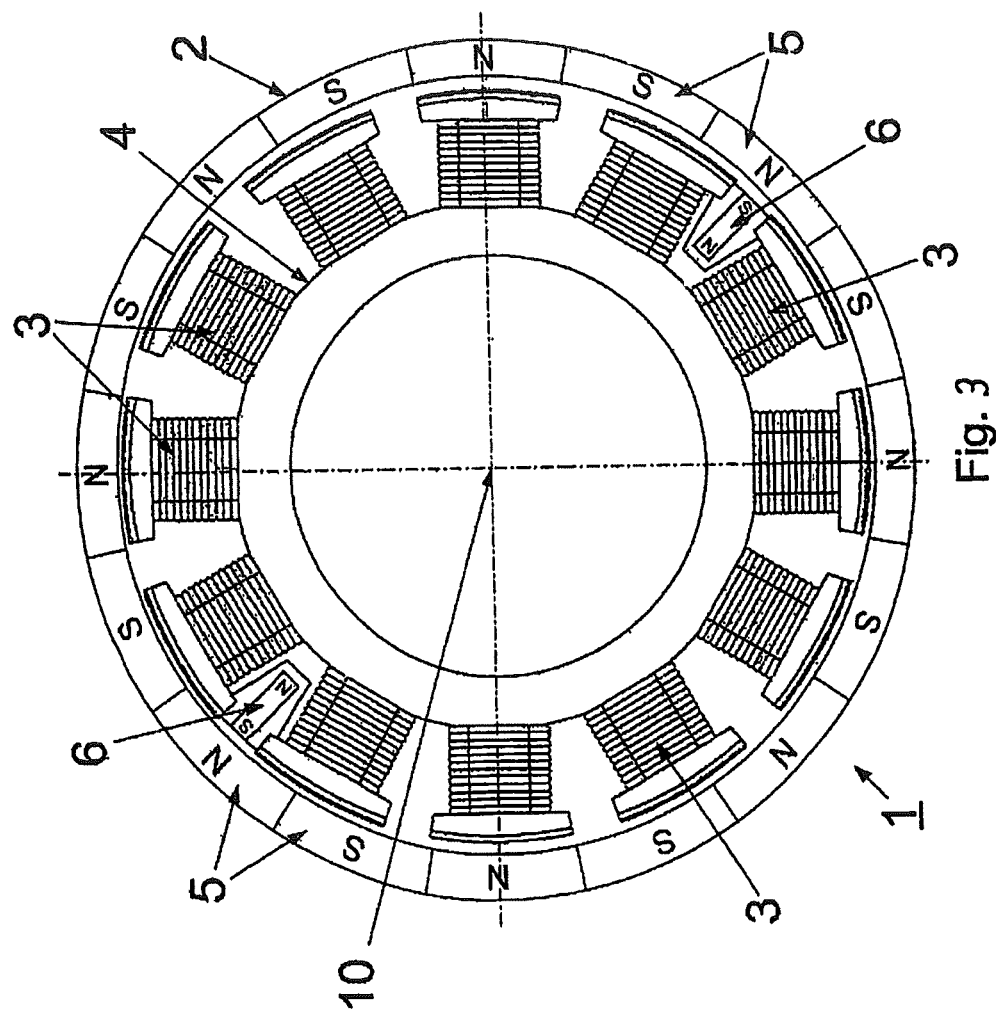

An illustrative embodiment of the invention is explained in more detail below with reference to the attached drawing, in which:

FIG. 1 shows a schematic view of a drive as internal rotor;
FIG. 2 shows an example of use in the form of a prosthetic arm; and
FIG. 3 shows a drive as external rotor.

FIG. 1 shows a schematic view of a drive 1 of an adjusting device with a stator 4, on the inner circumference of which exciter coils 3 are arranged. In the present case, twelve exciter coils 3 are provided and are arranged uniformly about the circumference of the stator 4. A rotor 2, which has a plurality of permanent magnets 5 of different polarity, is arranged inside the stator 4. The outer poles of the armature magnets 5 have alternating polarities. The rotor 2 turns about a rotation axis 10 when a rotary field is applied by the exciter coils 3. In the illustrative embodiment shown, two holding magnets 6 in the form of permanent magnets are arranged between two exciter coils 3 and generate a cogging torque, without energy having to be supplied. The armature magnets 5 then orient themselves according to their polarity opposite the holding magnets 6, and slight turns of the rotor 2 about the rotation axis 10 can take place. After the exciter coils 3 have been switched off, the rotor 2 is held in the respective position via the holding magnets 6, such that, for example after a prosthetic hand has been closed, the gripping force is maintained without additional expenditure of energy, even after the exciter coils 3 have been switched off.

In the illustrative embodiment shown, two holding magnets 6 are arranged lying opposite each other. In principle, further holding magnets 6 can also be arranged between the exciter coils 3. It is likewise possible to provide adequate cogging torque with just one holding magnet 6, if the magnetic field strength is sufficient.

In order to compensate for the cogging torque increased by the holding magnets 6 during the normal operation of the drive 1, a constant field can be superposed, by electromagnets (not shown), on the magnetic field of the holding magnets 6, such that no periodically occurring variations occur in the running of the motor.

The electromagnetic barrier effected by the holding magnets 6 can be obtained at very low cost and is practically free of wear, as a result of which the maintenance costs are kept low.

FIG. 2 shows a schematic view of a prosthetic arm, with an upper arm socket 11 that can be secured to an upper arm stump. A lower arm socket 12 is secured in an articulated manner on the upper arm socket 11, and a prosthetic hand 13 is in turn arranged at the distal end of the lower arm socket 12. A drive 1, as has been described above, is arranged between the upper arm socket 11 and the lower arm socket 12. With such a drive 1, it is possible to pivot the lower arm socket 12 relative to the upper arm socket 11 in a controlled manner. The pivoting can take place, for example, on the basis of myoelectric signals or another control device. When the lower arm socket 12 is in the desired position relative to the upper arm socket 11, the drive is switched off. By way of the holding magnets 6 arranged in the drive 1, it is possible to provide an increased cogging torque of the drive 1, such that the lower arm socket 12 can be held in the position relative to the upper arm socket 11. It is at least possible to increase the cogging torque to such an extent that the lower arm socket 12, together with the prosthetic hand 13, does not move relative to the upper arm socket 11 without external forces, and a holding function can thus be provided counter to the force of gravity and to the inertial forces that occur during the customary movements.

An additional form-fit lock, which may be necessary in some cases, can be provided in the joint between the upper arm socket 11 and the lower arm socket 12.

Likewise, a drive 1 comprising holding magnets 6 can be arranged in the joint between the lower arm socket 12 and the prosthetic hand 13, such that a rotation movement of the prosthetic hand 13 relative to the lower arm socket 12 can take place when the drive 1 is activated, and a locking action takes place, i.e. the cogging torque is increased, when the drive 1 is switched off. Here too, one or more additional locking mechanisms can be provided in order to fix the position of the prosthetic hand 13 relative to the lower arm socket 12.

FIG. 3 shows a variant of the invention, in which the drive 1 is designed as an external-rotor motor. The permanent magnets 5 with alternating polarity are arranged in a ring around the stationary exciter coils 3. The holding magnets 6 are again arranged between the exciter coils 3 and effect the additional cogging torque for the rotor 2. The permanent magnets 5 can be arranged in a bell or in a carrier via which the rotation torque is taken off and delivered for example to a gear.

It is also possible that the drive can be operated the opposite way round both according to FIG. 1 and also according to FIG. 3, i.e. that the permanent magnets 5 are fixed and are located on the stator 4, and that the exciter coils 3 turn together with the holding magnets 6 and are arranged on the rotor 2. In this way, the variant according to FIG. 1 would become an external rotor, and the variant according to FIG. 3 an internal rotor.

The invention claimed is:

1. An adjusting device for use with a prosthetic device, the adjusting device comprising a drive for adjusting at least one first component of the prosthetic device relative to a second component, wherein the drive is designed as a permanent-magnet electric motor and has a stator with exciter coils and a rotor with at least one permanent magnet as armature magnet, wherein at least one holding magnet in the form of a permanent magnet is arranged on the stator in order to provide a cogging torque for the rotor.

2. The adjusting device as claimed in claim 1, wherein a plurality of holding magnets are arranged, spaced apart from one another, on the stator.

3. The adjusting device as claimed in claim 1, wherein a plurality of armature magnets are arranged in the rotor, with alternating polarity about a circumference of the rotor.

4. The adjusting device as claimed in claim 1, wherein devices are provided for superposing a rotary field of the adjusting device with a constant magnetic field for compensation of the cogging torque during adjustment of the adjusting device.

5. A prosthetic device with an adjusting device as claimed in claim 1.

6. The prosthetic device as claimed in claim 5, wherein the prosthetic device is designed as a prosthetic hand or a prosthetic elbow.

7. The prosthetic device as claimed in claim 5, wherein the first component is a prosthetic finger and the second component is a chassis.

8. The prosthetic device as claimed in claim 7, wherein the drive is mounted on the chassis and is coupled to the prosthetic finger via a gear.

9. A method for operating an adjusting device as claimed in claim 1, wherein, when a rotary field is applied to drive the rotor, at least one constant field is superposed on the rotary field, such that the cogging torque generated by the holding magnet or the holding magnets compensated.

10. An adjusting device for use with a prosthetic device, the adjusting device comprising:
 a drive for adjusting at least one first component of the prosthetic device relative to a second component, wherein the drive is configured as a permanent-magnet electric motor and comprises:
  a stator having a plurality of circumferentially spaced apart exciter coils;
  a rotor having at least one permanent magnet configured as at least one armature magnet;
  at least one holding magnet in the form of a permanent magnet being arranged on the stator in order to provide a cogging torque for the rotor.

11. The adjusting device as claimed in claim 10, wherein the at least one holding magnet includes a plurality of holding magnets spaced apart from one another on the stator.

12. The adjusting device as claimed in claim 10, wherein the at least one armature magnet includes a plurality of armature magnets arranged in the rotor with alternating polarity about a circumference of the rotor.

13. The adjusting device as claimed in claim 10, wherein the drive is configured for superposing a rotary field of the adjusting device with a constant magnetic field for compensation of the cogging torque during adjustment of the adjusting device.

14. The adjusting device as claimed in claim 10, wherein the at least one holding magnet includes first and second holding magnets spaced apart on opposite sides of the rotor.

15. The adjusting device as claimed in claim 10, wherein the at least one first component comprises a prosthetic finger and the second component comprises a chassis of the prosthetic device.

16. The adjusting device as claimed in claim 10, wherein when a rotary field is applied to drive the rotor, at least one constant field is superposed on the rotary field, such that the cogging torque generated by the holding magnet or the holding magnets is compensated.

17. An adjusting device, comprising:
 a permanent-magnet electric motor configured to adjust at least one first component of a prosthetic device relative to a second component of the prosthetic device, wherein the motor comprises:
  a stator having a plurality of exciter coils;
  a rotor having at least one permanent magnet as an armature magnet;
  at least one holding magnet in the form of a permanent magnet, the at least one holding magnet being arranged on the stator to provide a cogging torque for the rotor.

18. The adjusting device as claimed in claim 17, wherein the at least one holding magnet includes a plurality of holding magnets spaced apart from one another on the stator.

19. The adjusting device as claimed in claim 17, wherein the armature magnet includes a plurality of armature magnets arranged in the rotor with alternating polarity about a circumference of the rotor.

* * * * *